(12) United States Patent
De Clerck

(10) Patent No.: US 8,388,342 B2
(45) Date of Patent: Mar. 5, 2013

(54) DRILL JIG FOR POSITIONING DENTAL IMPLANTS

(75) Inventor: René De Clerck, Tervuren (BE)

(73) Assignee: Dental Vision BVBA, Tervuren (BE)

( * ) Notice: Subject to any disclaimer, the term of this patent is extended or adjusted under 35 U.S.C. 154(b) by 182 days.

(21) Appl. No.: 12/374,655

(22) PCT Filed: Jul. 20, 2007

(86) PCT No.: PCT/BE2007/000093
§ 371 (c)(1),
(2), (4) Date: Jan. 21, 2009

(87) PCT Pub. No.: WO2008/009080
PCT Pub. Date: Jan. 24, 2008

(65) Prior Publication Data
US 2010/0209868 A1  Aug. 19, 2010

(30) Foreign Application Priority Data

Jul. 20, 2006  (EP) .................................. 06447095
Oct. 25, 2006  (EP) .................................. 06122964

(51) Int. Cl.
*A61C 8/00* (2006.01)
(52) U.S. Cl. ........................................ 433/174; 433/75
(58) Field of Classification Search .................. 433/34, 433/72, 74–76, 172–176
See application file for complete search history.

(56) References Cited

U.S. PATENT DOCUMENTS

| 3,445,935 | A | * | 5/1969 | Marshall .......................... 433/51 |
| 3,896,548 | A | * | 7/1975 | Zahn ............................... 433/74 |
| 5,556,278 | A | * | 9/1996 | Meitner ........................... 433/75 |
| 5,797,741 | A | | 8/1998 | Bonpard et al. |
| 5,888,034 | A | * | 3/1999 | Greenberg ................. 408/115 R |
| 5,954,769 | A | * | 9/1999 | Rosenlicht ................ 623/16.11 |
| 5,967,777 | A | * | 10/1999 | Klein et al. ..................... 433/75 |
| 6,206,696 | B1 | | 3/2001 | Day |
| 2003/0054318 | A1 | | 3/2003 | Gervais et al. |
| 2003/0224322 | A1 | * | 12/2003 | Kumar et al. ................ 433/141 |
| 2005/0170311 | A1 | | 8/2005 | Tardieu et al. |
| 2005/0266379 | A1 | * | 12/2005 | Kumar et al. ................ 433/141 |

FOREIGN PATENT DOCUMENTS

DE  10320709 A1  12/2004
WO   9926540 A    6/1999

* cited by examiner

Primary Examiner — Cris L Rodriguez
Assistant Examiner — Eric Rosen
(74) Attorney, Agent, or Firm — Browdy and Neimark, PLLC

(57) ABSTRACT

The invention relates to a template for placing at least one dental implant (7) in a jaw (1) having at least one bore (3) for guiding this implant (7) when it is fixed in the jaw (1), whereby a recess (4) is provided that opens at least partly in said bore (3) in order to enable verifying the position of a implant guide with the implant.

10 Claims, 3 Drawing Sheets

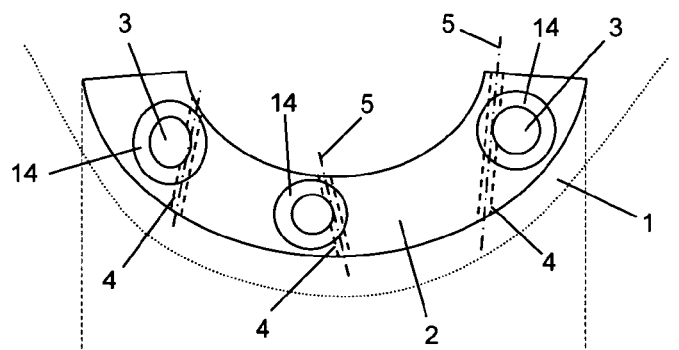
Fig. 1
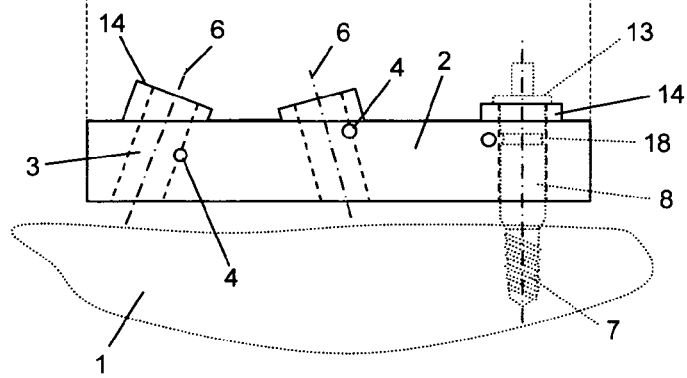
Fig. 2
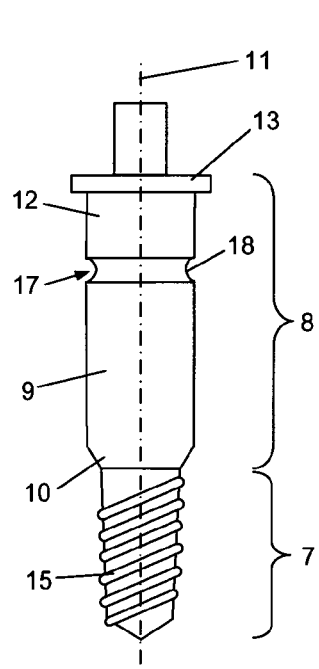
Fig. 3
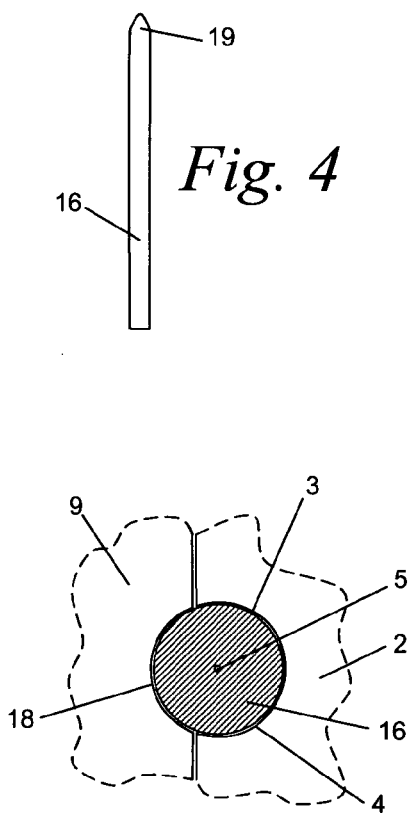
Fig. 4
Fig. 5
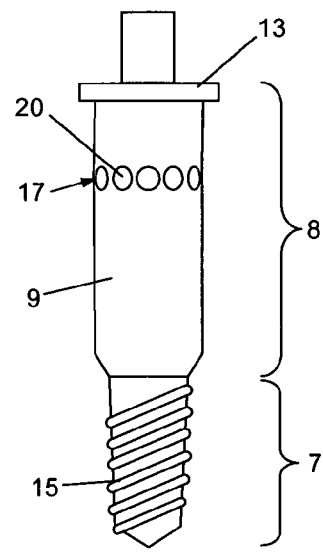
Fig. 6

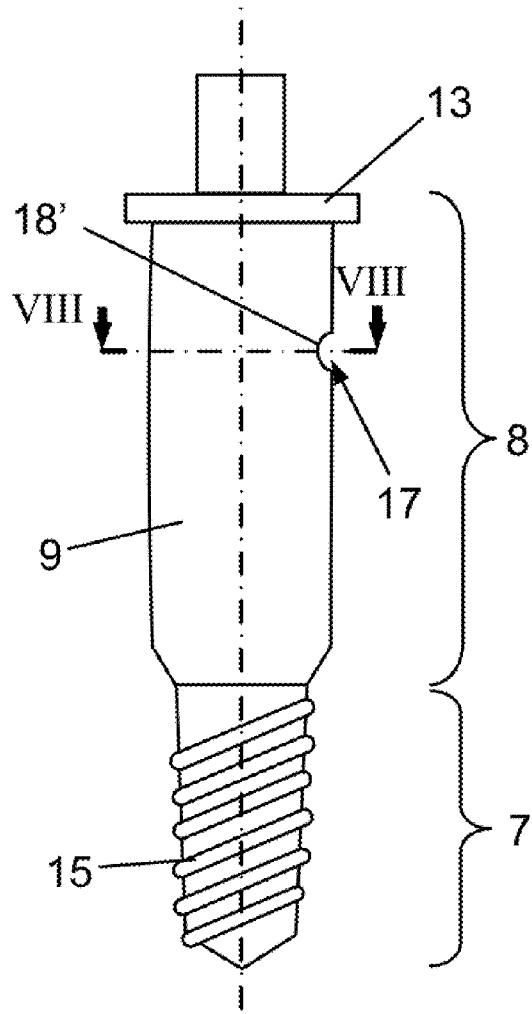
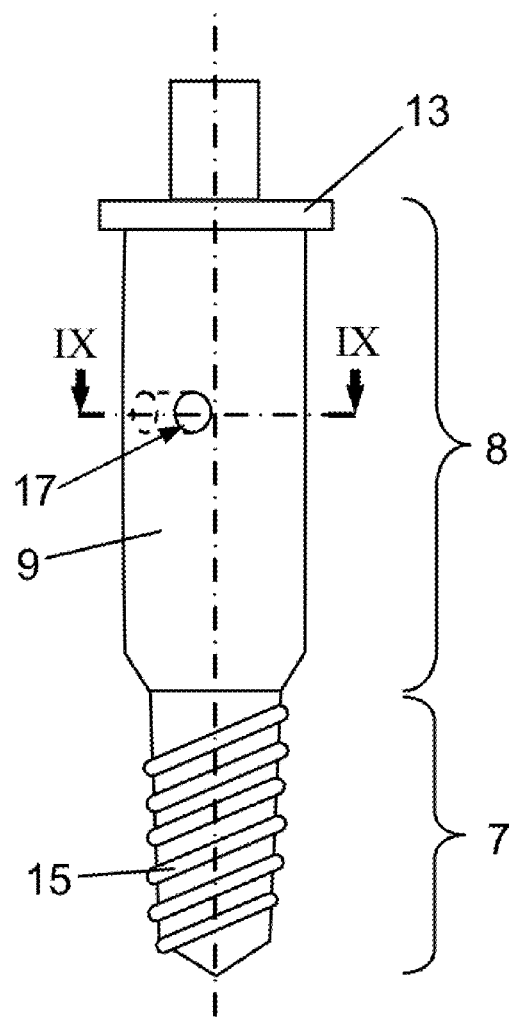
Fig. 7     Fig. 9
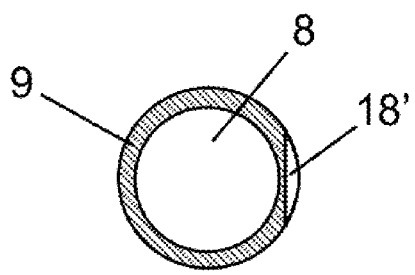
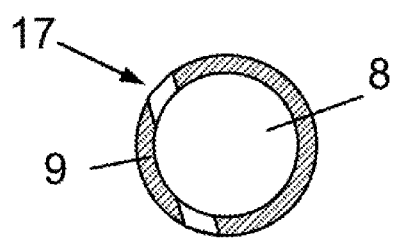
Fig. 8     Fig. 10

DRILL JIG FOR POSITIONING DENTAL IMPLANTS

The invention concerns a template for providing at least one dental implant in a jaw with at least one bore for guiding this implant when it is fixed in the jaw.

Further, the invention also concerns a set with a template, a blocking element and an implant guide for providing at least one dental implant in a jaw.

Such dental implants are put in a person's upper or lower jaw so as to form an anchorage for fixing a prosthetic element in the oral cavity such as for example a crown, what is called a bridge or a set of dentures, either or not complete.

When putting in a dental implant, a bore hole must be made in the jaw to fix the implant in. Normally, the implant is threaded and thus it is fixed in the bore hole by screwing it in the bore hole.

The selection of the position and orientation of the implant in the jaw depends among others on the shape and structure of the jaw. Especially the anatomical bone structure of the jaw must be taken into account, as well as the exact location of nerve bundles and blood vessels. Thus, when making a bore hole in the jaw or when putting in the implant, one must avoid damaging the nerve bundles and blood vessels. Further, one must make sure that the volume of the bone round the implant is sufficiently large so as to be able to strongly anchor the implant in the jaw.

According to the present state of the art, the desired position of an implant is determined by taking an image of the jaw and the nerve bundles and blood vessels that are present by means of an imaging system such as for example a CT scan. Based on this image, a position is selected for the implant which is as optimal as possible.

In order to be able to make the bore hole for providing the implant in the jaw with great accuracy according to the selected position and orientation, a custom-made template is made according to techniques known as such. Such techniques are based for example on a plaster mould, the use of CAD CAM or rapid prototyping.

Said template is then positioned on the jaw and possibly fixed to it in a detachable manner. Then, a bore hole is made in the jaw whereby the bore is guided through the template, and the implant together with what is called an implant guide is fixed in said bore hole in the jaw via the template.

An implant guide, also called "implant holder" or "fixture driver" among professionals, comprises a cylindrical body which is fixed in a detachable manner to the implant with one far end and which is co-axial to the latter. Such an implant guide forms an extension piece for the implant so as to guide it through said bore of the template into the jaw.

When providing an implant, it is of major importance that not only the actual position and orientation of the provided implant correspond almost exactly to the desired position and orientation thereof, but it is also of paramount importance that it is provided in the jaw at an exact depth.

According to the present state of the art, we try to realize this by providing a ring-shaped collar on the implant guide which, as soon as the desired depth of the implant has been reached, rests on a stop of the template provided to that end.

It is found, however, that it is very difficult to provide an implant at the desired depth when using such a system. In particular, it turns out that, as the implant is screwed in the jaw, the template becomes somewhat deformed when said collar makes contact with the above-mentioned stop, whereby the implant is screwed too deep in the jaw. If the implant is provided not deep enough, there will be no or less deformation of the template, but the implant will not be positioned correctly in relation to the other implants.

If, subsequently, a second implant is fixed in the jaw by means of the same template, the position and orientation of the corresponding bore of the template will have altered somewhat due to its deformation, such that this second implant can no longer be provided with the required accuracy.

One tries to avoid this situation by visually establishing, with the naked eye, when said collar makes contact with the above-mentioned stop as the implant is being screwed in the jaw. However, the result is not satisfactory, since in many cases the implant is nevertheless provided too deeply or not deeply enough.

People try nowadays to manufacture a dental prosthesis, in particular a set of dentures, on the basis of an electronic image of the jaw which is generated, for example, by making a CT scan. Such a prosthesis is normally fixed to the implants immediately after they have been provided.

If implants are not fixed in a jaw exactly in the desired, pre-determined position, depth or orientation, it will be practically impossible to fix the prosthesis to the implants.

The invention aims to remedy these disadvantages by providing a template which makes it possible to fix implants almost exactly in the required position, orientation and depth in a jaw without any deformation of the template occurring, whereby this template makes sure that one can detect with very great accuracy when an implant has reached a desired depth in the jaw.

To this aim, the template according to the invention is provided with a recess which opens at least partly in said bore.

Practically, said recess opens at the surface of the template on the one hand, and at least partly in said bore on the other hand.

According to a preferred embodiment of the template according to the invention, the longitudinal axis of said recess extends practically at right angles to the longitudinal axis of said bore.

According to an advantageous embodiment of the template according to the invention, the central axis of said recess is situated outside the volume of said bore, whereby a part of the volume of said recess is situated within the volume of the bore.

The invention also concerns a set with a template, a blocking element and an implant guide for providing at least one dental implant in a jaw, whereby the template has at least one bore for guiding said implant guide when putting an implant in the jaw. This set is characterised in that said template has a recess in which the above-mentioned blocking element can be inserted and which opens in said bore. The blocking element can be moved in the recess, such that it extends at least partly in said bore, whereby said implant guide is provided with a fixing part which works in conjunction with said blocking element so as to fix the implant guide in a pre-determined position in the template.

Other particularities and advantages of the invention will become clear from the following description of a preferred embodiment of the invention; this description is given as an example only and does not restrict the scope of the claimed protection in any way; the figures of reference used hereafter refer to the accompanying drawings.

FIG. 1 is a schematic top view of a template according to a preferred embodiment of the invention.

FIG. 2 is a schematic front view of the template from FIG. 1.

FIG. 3 is a schematic elevation of an implant and an implant guide according to a preferred embodiment of the invention.

FIG. 4 is a schematic elevation of a blocking element according to a preferred embodiment of the invention.

FIG. 5 is a schematic cross section of a blocking element and a part of a template and of an implant guide according to the invention.

FIG. 6 is a schematic elevation of an implant and an implant guide according to an interesting embodiment of the invention.

FIG. 7 is a schematic elevation of an implant and an implant guide according to another embodiment of the invention.

FIG. 8 is a schematic cross section of the implant holder from FIG. 7 according to line IIX-IIX.

FIG. 9 is a schematic elevation of an implant and an implant guide according to a variant of the embodiment from FIG. 7.

FIG. 10 is a schematic cross section of the implant holder from FIG. 9 according to line IX-IX.

Figure 11:
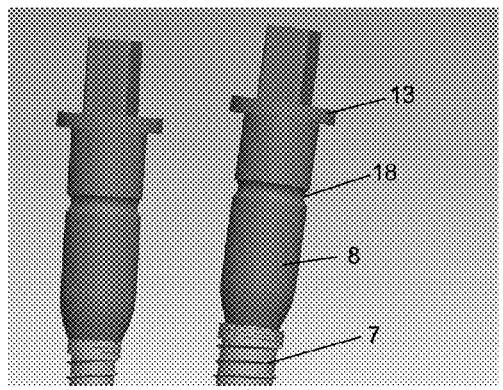
FIG. 11 is a schematic view in perspective of two implant guides according to the invention.

In the different figures, the same figures of reference refer to the same or analogous elements.

The invention concerns among others a template for providing dental implants in a person's jaw. Such a template is custom-made for the person to be treated and is represented very schematically in FIGS. 1 and 2. These figures also represent a part of a jaw 1, on which the template 2 is placed, represented by means of a dotted line.

The template 2 is manufactured by means of techniques known as such, for example milling or rapid-prototyping techniques. The template 2 can also be made by preparing what is called a plaster mould of the jaw 1 in which are provided auxiliary means representing the desired position and orientation of the implants to be provided. Onto this plaster mould is then provided a synthetic material which can form the template after it has cured.

In the template 2 are provided bores 3 which make it possible to guide a drill on the one hand so as to make an appropriate bore hole in the jaw 1 to put in an implant and to guide this implant when it is fixed in the bore hole on the other hand. Thus, such a template 2 allows to provide implants in a jaw 1 in a pre-determined position and at a pre-determined depth and according to a pre-selected orientation.

In order to make sure that the template 2 assumes a fixed and pre-selected position in relation to the jaw 1, it preferably has means to be fixed to said jaw 1 in a detachable manner. For clarity's sake, these means are not represented in the drawing, but they are known as such by the professional. Such means have already been described for example in document WO 03/003933.

According to the invention, the template 2 has at least one recess 4 which opens at least partly in one of said bores 3. In FIGS. 1 and 2, such a recess 4 opens into every bore 3. These recesses 4 have a circular cross section and they are in particular cylindrical.

The recesses 4 open at the surface of the template 2 on the one hand, and at least partly in said bores 3 on the other hand. As represented in FIG. 2, these recesses 4 preferably open on the side of the template 2 directed to the front of the person concerned and are thus easily accessible via the mouth opening when the template 2 is fixed to the jaw 1 in the oral cavity.

Further, the longitudinal axis of the central axis 5 of the cylindrical recesses 4 extends practically perpendicular to the longitudinal axis of the central axis 6 of said bores 3.

FIG. 3 represents an implant 7 onto which an implant guide 8 is fixed in a detachable manner. This implant guide 8 consists of a cylindrical body 9 which thus has means for fixing it in a detachable manner to the implant 7 with a first far end 10. The axis of the implant 7 hereby practically coincides with the axis 11 of the above-mentioned cylindrical body 9.

On the second far end 12, opposite the first far end 10, the cylindrical body 9 has a collar 13. When the template 2 is manufactured, a stop 14 is provided round the far end of the bores 3 along which the implant 7 must be provided in the template 2. The position of this stop 14 is selected such that said collar 13 will rest on it as soon as the desired depth of the implant 7 is reached while it is being placed in the jaw 1 by means of the implant guide 8.

The diameter of the cylindrical body 9 practically corresponds to that of the above-mentioned bore 3, such that the implant guide 8 can be guided in and through the bore in a fitting manner.

In particular, the implant 7 is fixed in the jaw 1 by guiding it together with the implant guide 8 through a corresponding bore 3 of the template 2 while it is being rotated round the axis 11 thereof. Thus, the implant 7 is screwed down in the bore hole which has previously been formed. It is very difficult, however, to determine the exact moment at which the collar 13 makes contact with the corresponding stop 14 of the template 2 such that, through the operation of the screw thread 15 which is present on the surface of the implant 7, the implant 7 is often placed a little too deep, whereby the template 2 is deformed somewhat, or not deep enough, such that the position of the implant 7 is not correct in relation to the other implants which must be provided in the jaw 1 or which have already been provided in the jaw 1.

The invention makes it possible to avoid this by detecting when said implant guide 8 has reached the desired position in the template 2 by means of a blocking element 16, whereby the implant 7 mounted on this implant guide 8 is situated at the pre-determined and desired depth in the jaw 1.

To this end, the implant guide 8 is provided with a fixing part 17 in the form of a ring-shaped recess 18 extending over the surface of the above-mentioned cylindrical body 9, as represented in FIG. 3. The central axis of this ring-shaped recess 17 corresponds in particular to the axis 11 of the cylindrical body 9. Thus, the ring-shaped recess 17 forms a notch which extends over the entire perimeter of the implant guide 8.

FIG. 4 schematically represents the blocking element 16 which comprises a stick which is provided with a preferably somewhat round, pointed far end 19. The cross section of this stick is selected such that it can be pushed in an almost fitting manner in said recess 4. Also, this stick preferably has a circular cross section.

In order to detect whether the implant guide 8 has reached the desired position in the template 2, the above-mentioned blocking element 16 is put up to the implant guide 8, via the recess 4, which is situated in the bore 3. When screwing in the implant 7, a small pressure force is exerted on the blocking element 16 according to its longitudinal direction, such that the latter pushes against the cylindrical body 9 of the implant guide 8. As soon as the desired depth of the implant 7 has been reached, the fixing part 17 with said ring-shaped recess 18 will be situated opposite the recess 4, as a result of which the blocking element 16, under the influence of the pressure exerted on it, will move at least into said recess 18.

When said pressure force is exerted for example manually on the blocking element 16, it is observed that it suddenly moves when the desired depth of the implant 7 is reached.

In order to allow for an accurate detection, the cross section of the ring-shaped recess 18 is preferably selected such that it fits almost exactly on the blocking element 16. Thus, this recess 18 is confined for example by rotating the line of intersection between the cylindrical body 9 and a torus formed by a circle, having a diameter which corresponds to that of the blocking element 16, round the central axis 11 of this cylindrical body 9.

Preferably, the central axis 5 of the recess 4 is situated outside the volume of the bore 3, whereby a part of the volume of this recess 4 is situated within the volume of the bore 3. This is schematically represented in FIG. 5.

FIG. 5 represents a schematic cross section of the template 2 according to a plane which comprises the central axis 6 of a bore 3 and which is perpendicular to the central axis of the corresponding cylindrical recess 4 as soon as an implant guide 8 has reached the desired position in the bore 3. FIG. 2 schematically represents the implant 7 and the implant guide 8 in this desired position by means of a dotted line.

The cylindrical recess 4 preferably extends from the surface of the template 2 past the corresponding bore 3 such that, when the implant guide 8 has reached the desired position in the bore 3, the blocking element can extend along either side of said bore 3.

In this way, not only the desired position of the implant guide 8 is detected, but the template 2 is also fixed in a detachable manner in relation to the jaw 1 via the implant guide 8 and the corresponding implant which is screwed in the jaw 1. Such an additional fixation of the template 2 in relation to the jaw 1 makes it possible to make other bore holes and to provide other implants 7 with an increased accuracy.

Naturally, said fixing part 17 of the implant guide may assume all sorts of shapes. Thus, FIG. 6 represents an alternative embodiment of an implant guide according to the invention. This implant guide 8 is provided with a fixing part 17 which comprises a series of cylindrical recesses 20 extending along the perimeter of the cylindrical body 9. The central axes of these recesses 20 extend in particular according to diagonals of the cylindrical body 9. Thus, the blocking element 16 can penetrate into one of these recesses 20 when the implant guide 7 is situated in the desired position in relation to the template. In this case, said cylindrical recesses 4 extend radially in relation to the bores 3 of course.

According to yet another embodiment of the implant guide and the template according to the invention, said fixing part 17 of the implant guide 8 is formed of a recess which, as opposed to the embodiment of the implant guide represented in FIG. 3, extends over only a part of the perimeter of the implant guide 8.

In such an implant guide 8, as represented in FIGS. 7 and 8, the fixing part 17 is formed of a recess 18' provided in the lateral surface of the implant guide 8. When the implant guide 8, together with the implant 7, has been provided up to the pre-determined and desired depth in a person's jaw 1 along the template 2, this recess 18' will extend in the prolongation of the template's 2 recess 4, such that the above-mentioned blocking element 16 can be shifted in an almost fitting manner in the recess 17 via the recess 4.

Consequently, in this embodiment of the invention, it is possible to put the implant 7 in the jaw 1 according to a pre-determined angular position in relation to the axis thereof.

In this case, the height of the recess 4 according to the axis 6 of the bore 3 concerned is preferably somewhat larger than the diameter of the blocking element 16. In particular, the difference between this height of the recess 4 and the diameter of the blocking element 16 is for example equal to the distance over which the implant 7 is moved in case of a complete rotation round the axis thereof, or it is equal to half said distance. The diameter of the recess 18' in the implant guide 8 corresponds to that of the blocking element 16.

According to a variant of this embodiment, the length of the recess 18', seen in the direction of the axis 11 of the implant 7 or of the implant guide 8, is larger than the diameter of the blocking element 16, whereas the diameter of the template's 2 recess 4 corresponds practically to that of the blocking element 16. In an advantageous manner, this length of the recess 18' is almost equal to the distance over which the implant 7 is moved according to the axis 11 thereof in case of a rotation round this axis when the implant 7 is screwed in the jaw, or it may be equal, for example, to twice that distance.

This embodiment of the invention may be applied for example when providing a solitary implant 7 in a jaw 1. The head of such an implant 7 may then be provided with what is called an anti-rotation element for mounting a dental crown. The small inaccuracy as far as the depth of the implant 7 in the bone of the jaw 1 is concerned, which may be the result of the difference between the height of the recess 4 or of the fixing part 18' and the diameter of the blocking element 16, can then be simply adjusted by means of occlusional grinding on the crown.

The implant guide 8 hereby preferably has no collar 13, but this collar 13 is replaced by a corresponding mark provided on the implant guide 8. The practician providing the implant 7 can then select, to a limited extent, the depth of the solitary implant 7 in the jaw 1, taking into account the desired orientation of the above-mentioned anti-rotation element.

FIGS. 9 and 10 represent a variant of the last embodiment, whereby said recess 18' in the implant guide 8 is cylindrical and extends crosswise through the latter. The diameter of the recess 18' corresponds to that of the blocking element 16, such that the latter can be provided in the recess 18' in a fitting manner through a corresponding recess 4 of the template 2 as soon as the implant has reached a desired depth as well as the pre-determined angular position round the axis thereof.

The invention cannot only be applied by means of a template 2 that was made for example by means of a rapid-prototyping technique on the basis of a digital image of the jaw 1 which had been generated, for example, by means of a CT scan, but it can also be applied if a template is cast, for example, of plaster or a synthetic material.

In this case, replicas of implants are preferably put in a plaster mould of a jaw. On each of these replicas of the implants is then fixed an implant guide according to the invention. The implant guides are hereby each time surrounded by a cylindrical sleeve whose inner diameter corresponds to the outer diameter of the corresponding implant guide and whose central axis corresponds to that of the implant guide. Further, a corresponding blocking element is provided for these implant guides in the fixing part of the implant guide. This blocking element hereby extends through corresponding recesses which are provided in said sleeve.

According to a very interesting variant, said sleeve is fixed to a tube whose inner diameter corresponds practically to that of the blocking element 16. Thus, the whole of the sleeve and the tube form a prefab element, and this is pushed in a fitting manner over each of the implant guides of the plaster mould, whereby a blocking element is put through the tube in a fitting manner until it extends through said fixing part of the implant guide.

Next, the template according to the invention is made for example by casting a synthetic material and by letting it cure, such that said sleeves with the corresponding blocking elements or tubes are at least partly embedded in this synthetic material. After the curing, the implant guides and/or the blocking elements are removed from the formed whole, such that a template is obtained whereby said cylindrical sleeves form the bores 3 which have been described in the above-mentioned embodiments of the invention. The recess which is created by removing the blocking element from the cured synthetic material thus forms the above-mentioned recess 4. If, as mentioned above, the sleeve is fixed to a tube, said recess 4 is formed in the template 2 by the cylindrical space available in the tube.

Figure 12:
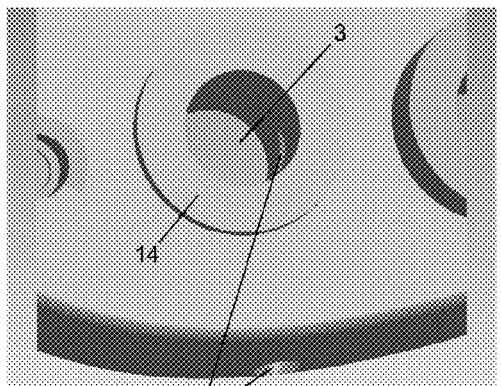
FIG. 12 is a schematic top view in perspective of a part of a template according to the invention.
Figure 13:
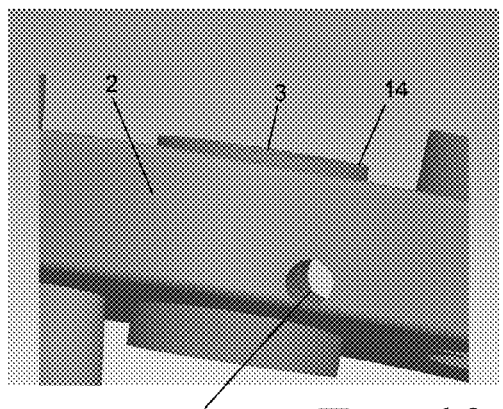
FIG. 13 is a schematic side view in perspective of the part of the template from FIG. 12.
Figure 14:
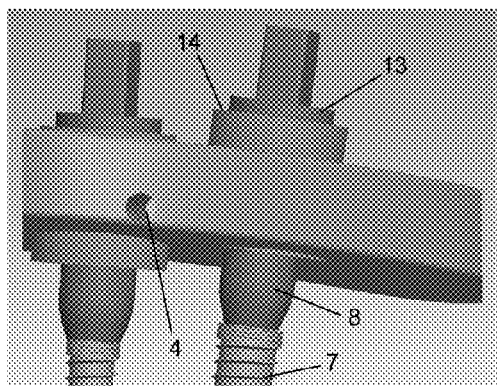
FIG. 14 is a schematic side view in perspective of a part of a template with two implant guides according to the invention.
Figure 15:
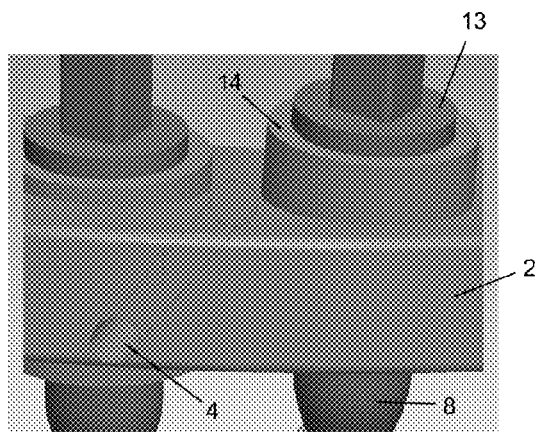
FIG. 15 is another view in perspective of the part of the template with two implant guides from FIG. 14.
Figure 16:
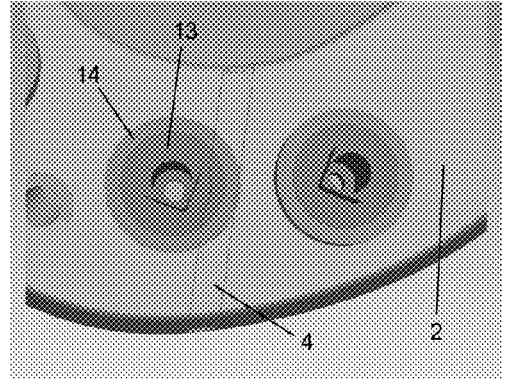
FIG. 16 is a schematic top view of the part of the template from FIGS. 14 and 15 with two implant guides.

FIGS. 11 to 16 represent schematic views in perspective to further illustrate the invention.

Naturally, the invention is not restricted to the embodiments of the template, the implant guide or the blocking element as described above and represented in the accompanying drawings. Thus, the blocking element may for example comprise a stick which works in conjunction with a compression spring so as to move it into the fixing part 17 when the desired position of the implant guide 8 has been reached.

Although, in the above-described embodiments of the invention, said recess 4 and said blocking element extend according to a straight line, it is also possible, for example, that the recess 4 is slightly bent, whereas the blocking element comprises a flexible stick or an elastic wire.

Further, the cross section of the recess 4 and/or of the blocking element is not necessarily circular, but it may have various shapes, for example elliptic, rectangular, etc. Preferably, the recess 4 presents a smooth internal surface and the blocking element also has a smooth surface. Preferably, the recess 4 has a smooth internal surface and the blocking element also has a smooth surface.

The invention claimed is:

1. Kit with a template (2), a blocking element (16) and an implant guide (8) for guiding at least one dental implant (7) together with the implant guide (8) while screwing the implant (7) in a jaw (1), wherein the implant guide (8) comprises a cylindrical body and is fixable in a detachable way with one far end to said implant (7) such that the cylindrical body is coaxial with the implant and wherein the template (2) has at least one bore (3) for guiding said implant guide (8) while screwing the implant (7) in the jaw (1), wherein said template (2) has a recess (4) in which said blocking element (16) can be inserted and which opens in said bore (3), whereby said blocking element (16) can be moved in the recess (4), such that the blocking element (16) extends at least partly in said bore (3), whereby said implant guide (8) is provided with a fixing part (17) formed of a recess (18,18',20) which works in conjunction with said blocking element (16) so as to fix the implant guide (8) in a pre-determined position in the template (2), and wherein the internal diameter of said bore (3) substantially corresponds to the external diameter of said implant guide (8) such that the implant guide (8) can be slid in a matching way along an axial direction of the implant guide (8) through said bore (3).

2. Kit according to claim 1, wherein the position of said recess (4) of the template (2) is selected such that, when said implant (7) has been definitely fixed in said jaw (1), the position of said recess of the template corresponds to the position of said fixing part (17) of the implant guide (8) which is fixed to the implant (7) in a detachable manner and which extends in said bore (3), such that said blocking element (16) can be provided in said recess (4) of the template up to said fixing part (17) so as to verify the position of the implant guide (8) in relation to the template (2) and, possibly, fix the implant guide (8) in a detachable manner in relation to the template (2).

3. Kit according to claim 1, wherein said implant guide (8) has a protrusion which must rest against a stop (14) of the template (2) when said implant (7) has been fixed in the jaw (1), wherein this stop (14) is provided on one far end of said bore (3) and wherein the distance between said protrusion and said fixing part (17) of the implant guide (18) is practically equal to the distance between the stop (14) and said recess (4) of the template (2), such that, when the implant (7) has been fixed in the jaw (1), the position of the implant guide (8) in relation to the template (2) can be verified by putting said blocking element (16) in said recess (4) of the template (2) up to the fixing part (17).

4. Kit according to claim 1, wherein means are provided for fixing said template (2) in a detachable manner to said jaw (1).

5. Kit according to claim 1, wherein a longitudinal axis (5) of said recess (4) of the template (2) extends practically perpendicular to the longitudinal axis (6) of said bore (3).

6. Kit according to claim 1, wherein said recess (4) of the template (2) has a circular cross section.

7. Kit according to claim 1, wherein a central axis (5) of said recess (4) of the template (2) is situated outside the volume of said bore (3), and wherein a part of the volume of said recess (4) of the template (2) is situated within the volume of the bore (3).

8. Kit according to claim 1, wherein said recess (4) of the template (2) opens at the surface of the template (2), and at least partly in said bore (3).

9. Kit according to claim 1, wherein said blocking element (16) comprises a cylindrical stick which can shift in an almost fitting manner in said recess (4) of the template (2) in a longitudinal direction of the recess (4).

10. Method for fixing a dental implant in a predetermined depth in a jaw, comprising:
   providing a template that has at least one bore for guiding the implant while fixing it in the jaw and wherein the template has a recess which opens at least partly in said bore;
   positioning the template on the jaw;
   guiding a drill through the bore so as to make a bore hole in the jaw;
   fixing an implant guide to the implant in a detachable manner with one far end such that the implant guide is coaxial to the implant, wherein the implant guide has a cylindrical body provided with a fixing part formed by a recess;
   fixing the implant in the bore hole in the jaw by guiding the implant together with the implant guide through the bore of the template, while exercising a pressure on a blocking element fitted in said recess of the template such that the blocking element pushes against the cylindrical body of the implant guide;
   detecting whether the implant guide has reached a desired position in the template, when the recess forming said fixing part is situated opposite the recess in the template, by moving the blocking element at least into said recess forming the fixing part of the implant guide under influence of said pressure exercised on the blocking element.

\* \* \* \* \*